United States Patent [19]

Dressel

[11] Patent Number: 5,102,410
[45] Date of Patent: Apr. 7, 1992

[54] SOFT TISSUE CUTTING ASPIRATION DEVICE AND METHOD

[76] Inventor: Thomas D. Dressel, 8725 Walton Oaks Cir., Bloomington, Minn. 55438

[21] Appl. No.: 577,679

[22] Filed: Oct. 9, 1990

Related U.S. Application Data

[63] Continuation-in-part of Ser. No. 485,081, Feb. 26, 1990, Pat. No. 4,985,027.

[51] Int. Cl.⁵ .............................................. A61B 17/36
[52] U.S. Cl. ..................................... 606/15; 606/17
[58] Field of Search ........................... 128/395–398, 128/749, 752; 606/3, 13–16, 45, 46, 49, 17

[56] References Cited

U.S. PATENT DOCUMENTS

| | | | |
|---|---|---|---|
| 3,858,577 | 1/1975 | Bass et al. | 606/15 |
| 4,169,984 | 10/1979 | Parisi | 128/24 A |
| 4,266,547 | 5/1981 | Komiya | 128/395 |
| 4,492,230 | 1/1985 | Sunago et al. | 606/13 |
| 4,515,583 | 5/1985 | Sorich | 604/22 |
| 4,531,934 | 7/1985 | Kossovsky et al. | 604/22 |
| 4,608,980 | 9/1986 | Aihara | 128/303.1 |
| 4,633,872 | 1/1987 | Chaffee et al. | 128/303.1 |
| 4,641,912 | 2/1987 | Goldenberg | 128/6 |
| 4,646,734 | 3/1987 | Cabrera et al. | 128/303.1 |
| 4,676,242 | 6/1987 | Doi | 128/303.1 |
| 4,735,605 | 4/1988 | Swartz | 604/22 |
| 4,775,365 | 10/1988 | Swartz | 604/119 |
| 4,784,649 | 11/1988 | Imonti et al. | 604/240 |
| 4,792,327 | 12/1988 | Swartz | 604/22 |
| 4,799,754 | 1/1989 | Godenberg | 128/6 |
| 4,834,703 | 5/1989 | Dubrul et al. | 604/48 |
| 4,857,063 | 8/1989 | Glenn | 604/317 |
| 4,863,439 | 9/1989 | Sanderson | 604/264 |
| 4,886,491 | 12/1989 | Parisi et al. | 604/22 |
| 4,955,882 | 9/1990 | Hakky | 606/14 |

FOREIGN PATENT DOCUMENTS 3209444  10/1982  Fed. Rep. of Germany ........ 606/14

*Primary Examiner*—Max Hindenburg
*Attorney, Agent, or Firm*—Faegre & Benson

[57] ABSTRACT

A laser soft tissue aspiration device comprises an aspiration cannula housing a laser energy transmitting means for conducting laser energy to the site within a patient's body for aspiration of soft tissue. The cannula is provided with an aspiration inlet port adjacent the cannula distal end. The proximal end of the cannula is provided with fluid flow connection to an aspiration source. A laser guide tube is additionally provided housing the laser energy transmitting means extending longitudinally within the cannula lumen from a laser energy source at the cannula proximal end and terminating at a point immediately prior to the aspiration inlet port. The tube also provides a conduit for transmitting cooling and cleaning fluid flow for the laser energy transmitting means.

A surgical method of aspirating soft tissue from a patient in vivo using this device is also provided transmitting means. Separated soft tissue and fluid is aspirated through the aspiration inlet port and the cannula by means of an aspiration source at the proximal end of the cannula.

9 Claims, 11 Drawing Sheets

SOFT TISSUE CUTTING ASPIRATION DEVICE AND METHOD

RELATED U.S. APPLICATION DATA

This application is a continuation-in-part of U.S. Ser. No. 07/485,081, filed Feb. 26, 1990, entitled SOFT TISSUE ASPIRATION DEVICE AND METHOD, now U.S. Pat. No. 4,985,027..

FIELD OF THE INVENTION

This invention relates to a device and method for improving the surgical procedure of soft tissue removal by aspiration and more particularly to a device and method utilizing laser energy to more readily and safely facilitate the separating of soft tissue from a patient in vivo. This invention has immediate and direct application to the surgical procedure of liposuction or body contouring as well as application in the surgical procedures of other soft tissue removal such as brain tissue, eye tissue, and other soft tissue inaccessible to other soft tissue aspiration techniques.

BACKGROUND OF THE INVENTION

Within the past decade, the surgical use of lasers to cut, cauterize and ablate tissue has been developing rapidly. Advantages to the surgical use of laser energy lie in increased precision and maneuverability over conventional techniques. Additional benefits include prompt healing with less post-operative pain, bruising, and swelling. Lasers have become increasingly important, especially in the fields of Ophthalmology, Gynecology and Dermatology, as a less invasive, more effective surgical therapeutic modality which allows the reduction of the cost of procedures and patient recovery times due to diminished tissue trauma, bleeding, swelling and pain. The $CO_2$ laser has achieved wide spread use in surgery for cutting and vaporizing soft tissue. The $CO_2$ laser energy has a very short depth of penetration, however, and does not effectively cauterize small blood vessels. Other means such as electrocautery must be used to control and minimize blood loss. The Neodymium-YAG laser, on the other hand, because of its greater depth of tissue penetration, is very effective in vaporizing soft tissue and cauterizing small blood vessels. But as a result of this great depth of tissue penetration, the Neodymium-YAG laser has achieved limited use in the field of soft tissue surgery because of the possibility of unwanted damage to deeper tissues in the path of the laser energy beam.

Liposuction, a surgical technique of removing unwanted fat deposits for the purpose of body contouring, has achieved widespread use. In the U.S., over 100,000 liposuction procedures were performed in 1989 alone. This technique utilizes a hollow tube or cannula with a blunt tip and a side hole or tissue aspiration inlet port near its distal end. The proximal end of the cannula has a handle and a tissue outlet port connected to a vacuum aspiration pump. In use, a small incision is made, the cannula tip and adjacent tissue inlet port is passed beneath the surface of the skin into the unwanted fat deposit. The vacuum pump is then activated drawing a small amount of tissue into the lumen of the cannula via the inlet port. Longitudinal motion of the cannula then removes the unwanted fat by a combination of sucking and ripping actions. This ripping action causes excessive trauma to the fatty tissues resulting in considerable blood loss and post-operative bruising, swelling and pain. Proposed advances in the techniques and apparatus in this field have been primarily directed to the design of the aspiration cannula, and more recently have involved the application of ultrasound and irrigation to melt and solubilize fatty tissue or the use of an auger, within the lumen of the cannula, to facilitate soft tissue removal. These proposed advances do not adequately address the goals of the surgical procedure: the efficient and precise removal of soft tissue with minimal tissue trauma and blood loss.

This invention utilizes a modification of a suction lipectomy cannula, already in clinical use, to position soft tissue within a protective chamber, allowing a Neodymium-YAG laser energy beam to cut and cauterize the soft tissue without fear of unwanted damage to surrounding or deeper tissues. This invention renders the removal of soft tissue safer, more precise, faster (and thus more efficient) and minimizes tissue trauma by eliminating the ripping action inherent in the conventional liposuction method.

This invention, by eliminating the ripping action of the conventional liposuction method, expands the scope of soft tissue removal. Currently, the liposuction method is limited to the aspiration of fat. Other soft tissues, such as breast tissue, lymphangiomas, and hemangiomas are too dense or too vascular to allow efficient and safe removal utilizing the liposuction method. This invention with the precise cutting and coagulating action of the Neodymium-YAG laser or other fiber delivered cautery and coagulating laser, within the cannula, Permits the removal of these dense or vascular soft tissues.

This invention, by controlling the depth of penetration of the Neodymium-YAG laser within the protective aspiration cannula, expands the surgical applicability of the Neodymium-YAG laser and other lasers. This laser can now be used, for example, in the precise removal of brain tissue without fear of unwanted damage to surrounding or deeper tissues. At this time, the $CO_2$ laser is extensively used for the vaporization of brain tumors, but because of its inability to effectively coagulate blood vessels, other methods such as electrocautery must be used to control blood loss during the procedure. In addition, because the vaporization of tissue generates large volumes of noxious and potentially toxic smoke, expensive, noisy and cumbersome suction devices must be used to eliminate the smoke from the surgical field. This invention, by utilizing the more effective coagulating power of the Neodymium-YAG laser, within the aspiration cannula, permits the combined action of tissue cutting, control of blood loss, and elimination of smoke from the surgical field.

The basic design of the present Soft Tissue Laser Aspiration Device of this invention can be scaled down to permit soft tissue aspiration in other parts of the body. For example, an appropriately sized version of the present device can be used for safe removal of scar tissue from within the eye or adjacent to the retina and lens tissue from within the eye. Other appropriately sized and scaled versions of the present device may also be used for the removal of other unwanted soft tissues within the body. For example: removal of unwanted tracheal tissue, such as bronchial adenomas; removal of polyps and other soft tissue from within the lumen of the gastrointestinal tract; for endometrial ablations within the uterus; in conjunction with laparoscopic techniques to remove endometrial tissue within the abdomen.

BRIEF DESCRIPTION OF THE INVENTION

This invention provides a soft tissue aspiration device comprising an aspiration cannula and a fluid and laser fiber guide tube extending longitudinally. The guide tube housing a laser energy transmitting fiber for conducting the laser energy to the soft tissue removal site within the patient's body and also housing a fluid flow path around the laser energy transmitting fiber. The aspiration cannula has a proximal and a distal end. The cannula is provided with a soft tissue aspiration inlet port adjacent to the cannula distal end. The proximal end of the cannula is attached to a handle which is provided with a fluid flow delivery port, a laser energy transmitting fiber inlet port, and an aspirated soft tissue outlet port. The fluid and laser fiber guide tube extends longitudinally from near the proximal end of the soft tissue aspiration device to a point immediately prior to the soft tissue aspiration inlet port within the cannula. A laser energy transmitting fiber extends from a laser energy source to the proximal end of the handle and longitudinally within the guide tube to a point immediately prior to the terminal point of the guide tube. Within the soft tissue aspiration device guide tube, the laser energy transmitting fiber is surrounded by fluid flow from a fluid source to the laser guide tube terminal point.

This invention also provides a surgical method of aspirating soft tissue from a patient in vivo using the device just described.

DETAILED DESCRIPTION OF THE INVENTION

A. The First Soft Tissue Aspiration Device; FIGS. 1-10

Figure 1:
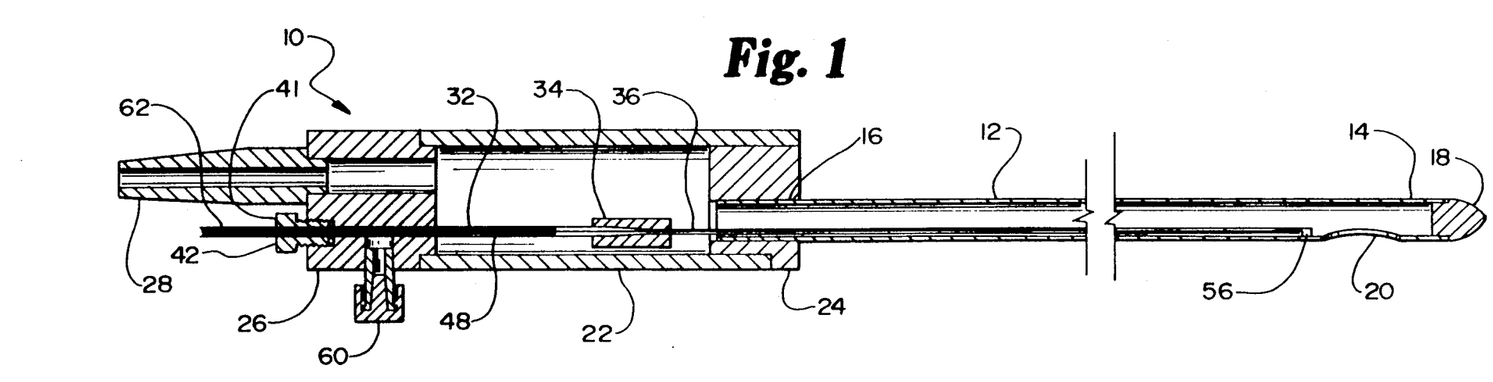
FIG. 1 is a side cut-away elevation view of a first soft tissue aspiration device of the present invention.
Figure 2:
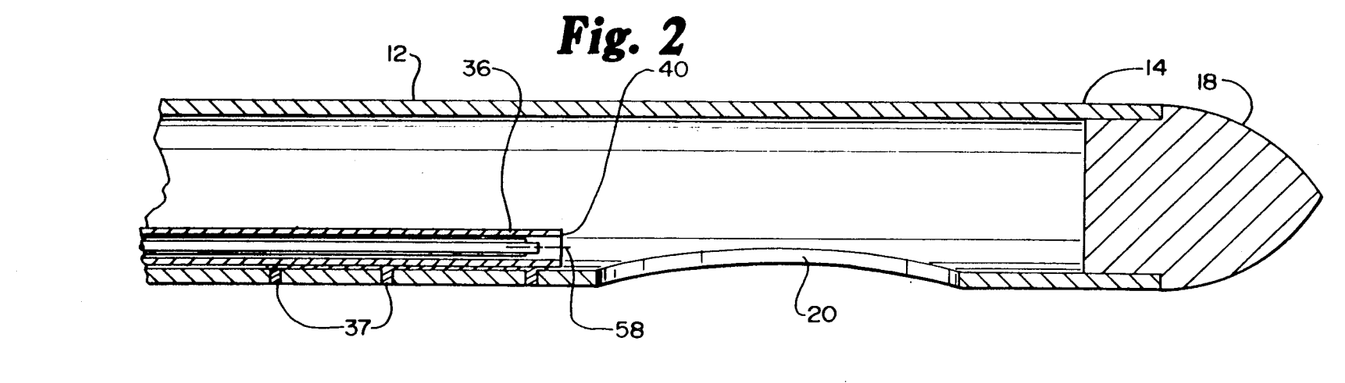
FIG. 2 is an exploded longitudinal section view of the distal end of the cannula of the device of FIG. 1.
Figure 7:
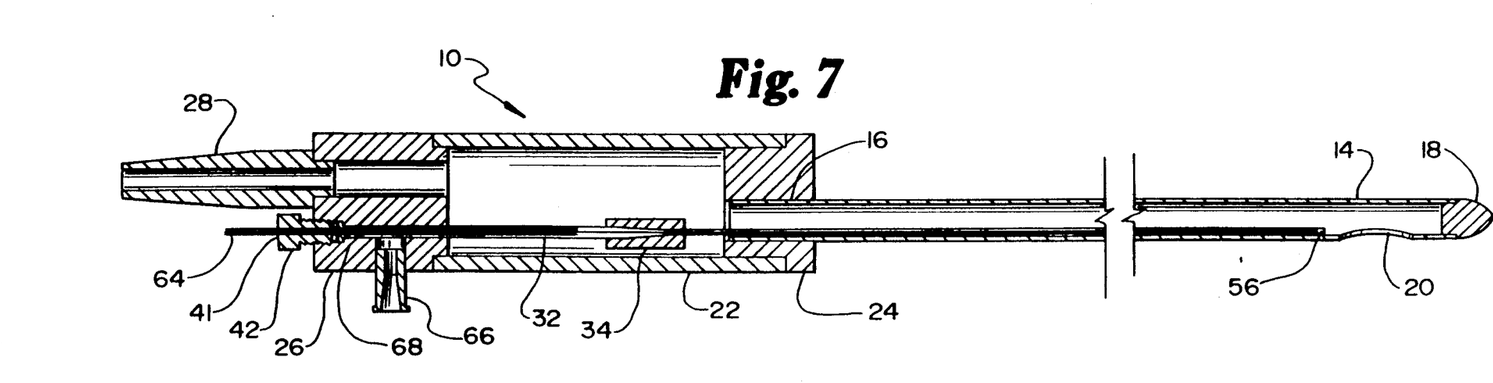
FIG. 7 is a side cut-away elevation view of the first soft tissue aspiration device showing the optional fluid delivery port and bushing for use with alternative fiber optic delivery system.
Figure 10:
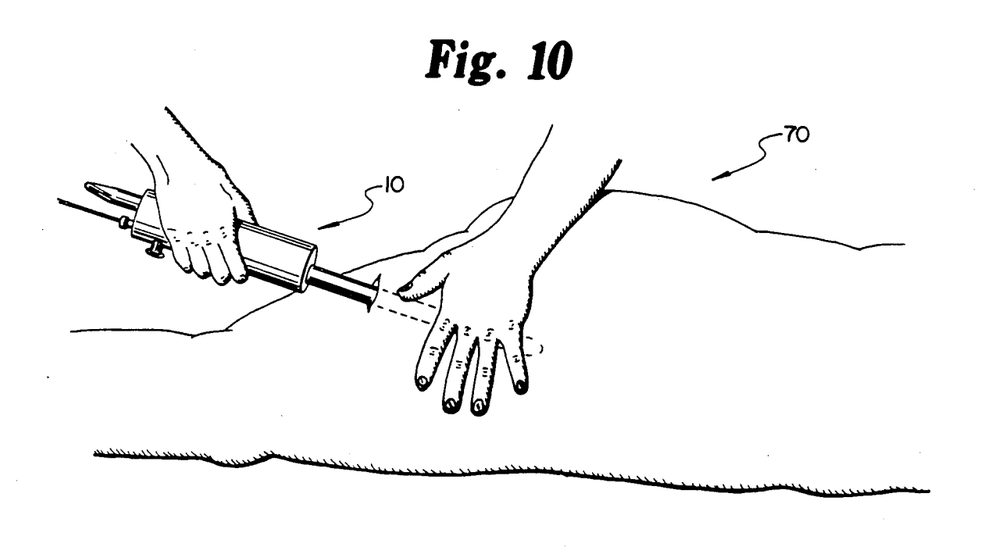
FIG. 10 is a cut-away detail of the first laser soft tissue device illustrated in position for performing liposuction within a fatty deposit of a body intermediate overlying epidermal layer and underlying muscle layer.

FIGS. 1, 7 and 10 illustrate a first laser soft tissue device 10 according to the present invention. The device 10 includes an aspiration cannula 12 having soft tissue inlet port 20 adjacent to the distal end 14 and cannula tip 18. As illustrated in FIGS. 1, 2 and 7, the cannula tip 18 can advantageously be a generally rounded, blunt or bullet shaped tip attached to the cannula 12 by welding or soldering. As illustrated in FIGS. 1 and 7, the cannula proximal end 16 is retained within the distal handle end cap 24, the aspirated soft tissue outlet port 28 is retained within the proximal handle end cap 26, and the distal handle end cap 24 and proximal handle end cap 26 are retained within the handle 22. The soft tissue outlet port is connected to an aspiration source by a plastic tubing (not shown).

Figure 3:
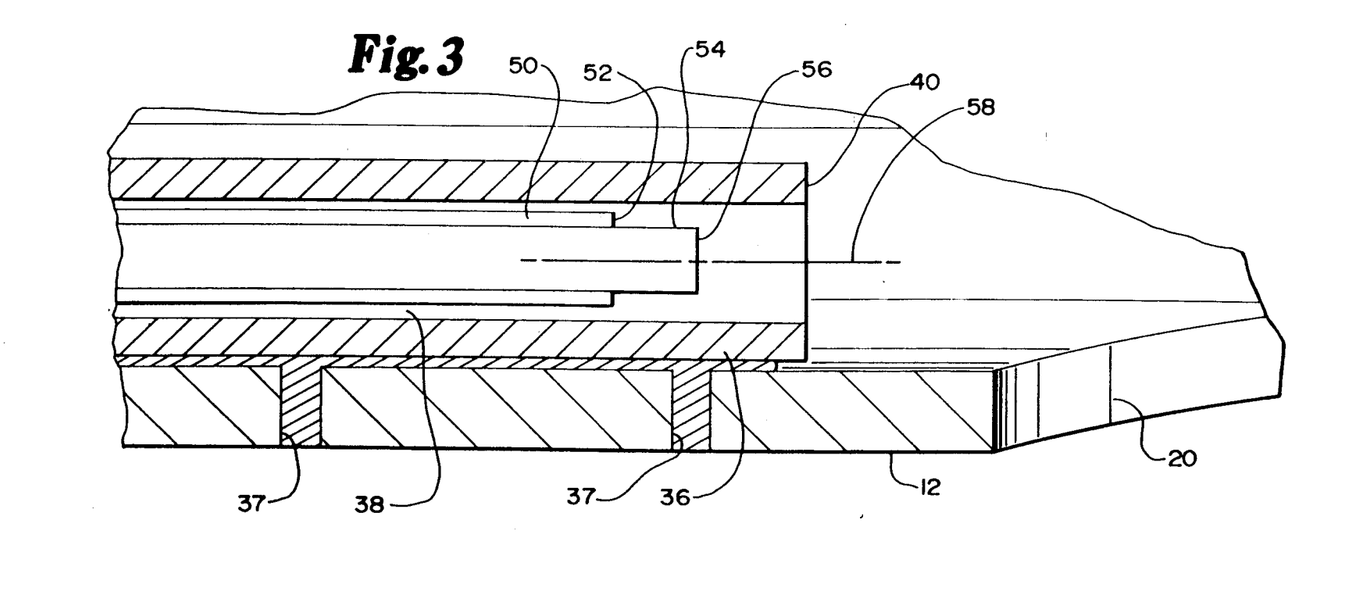
FIG. 3 is an exploded view similar to FIG. 2, showing the distal end of the laser fiber optic delivery system adjacent the soft tissue aspiration inlet port.
Figure 4:
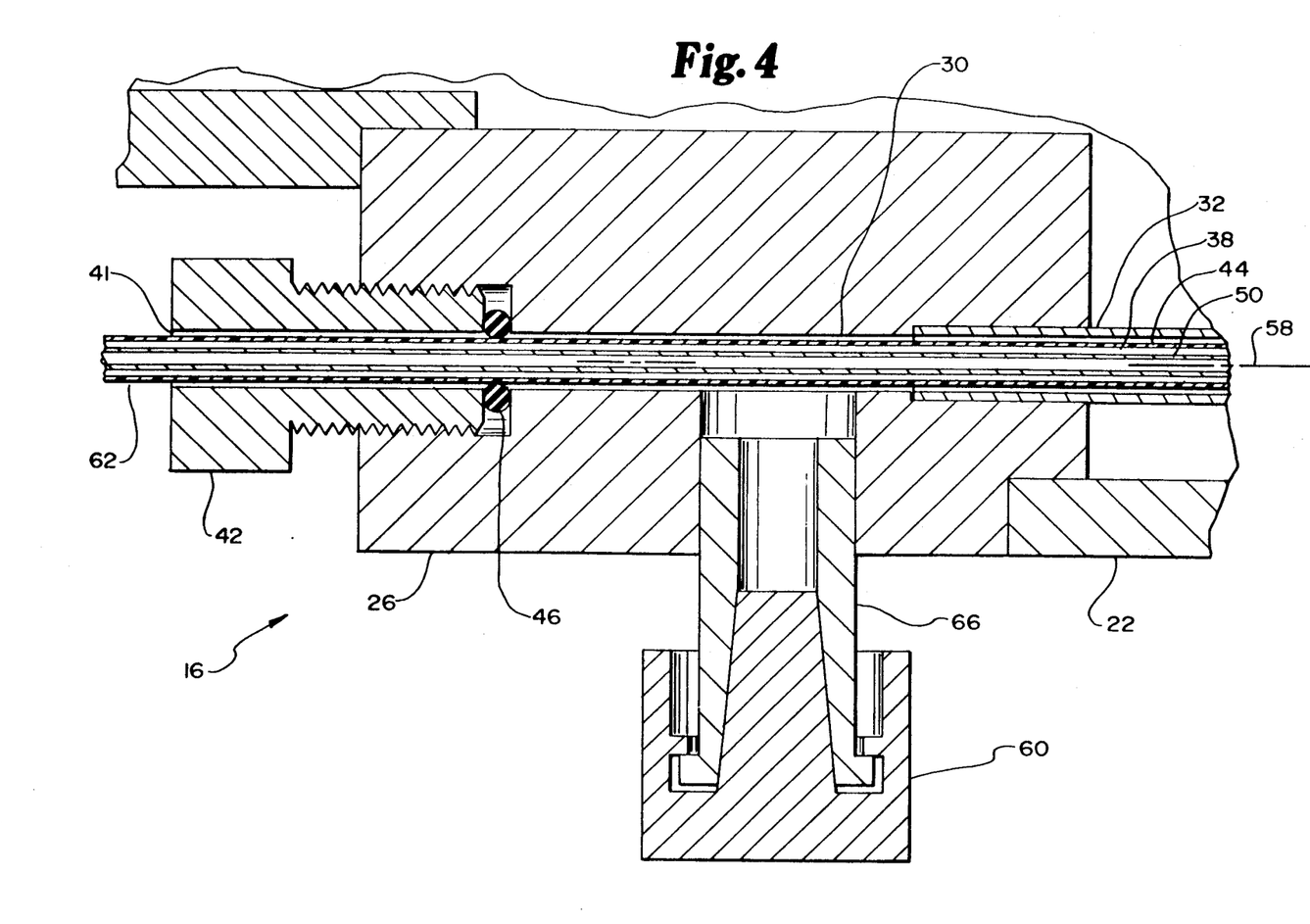
FIG. 4 is a partial exploded longitudinal section view of the handle and proximal end cap of the first device showing the attachments of the fluid and laser guide tube to the laser fiber and sources of fluid.
Figure 5:
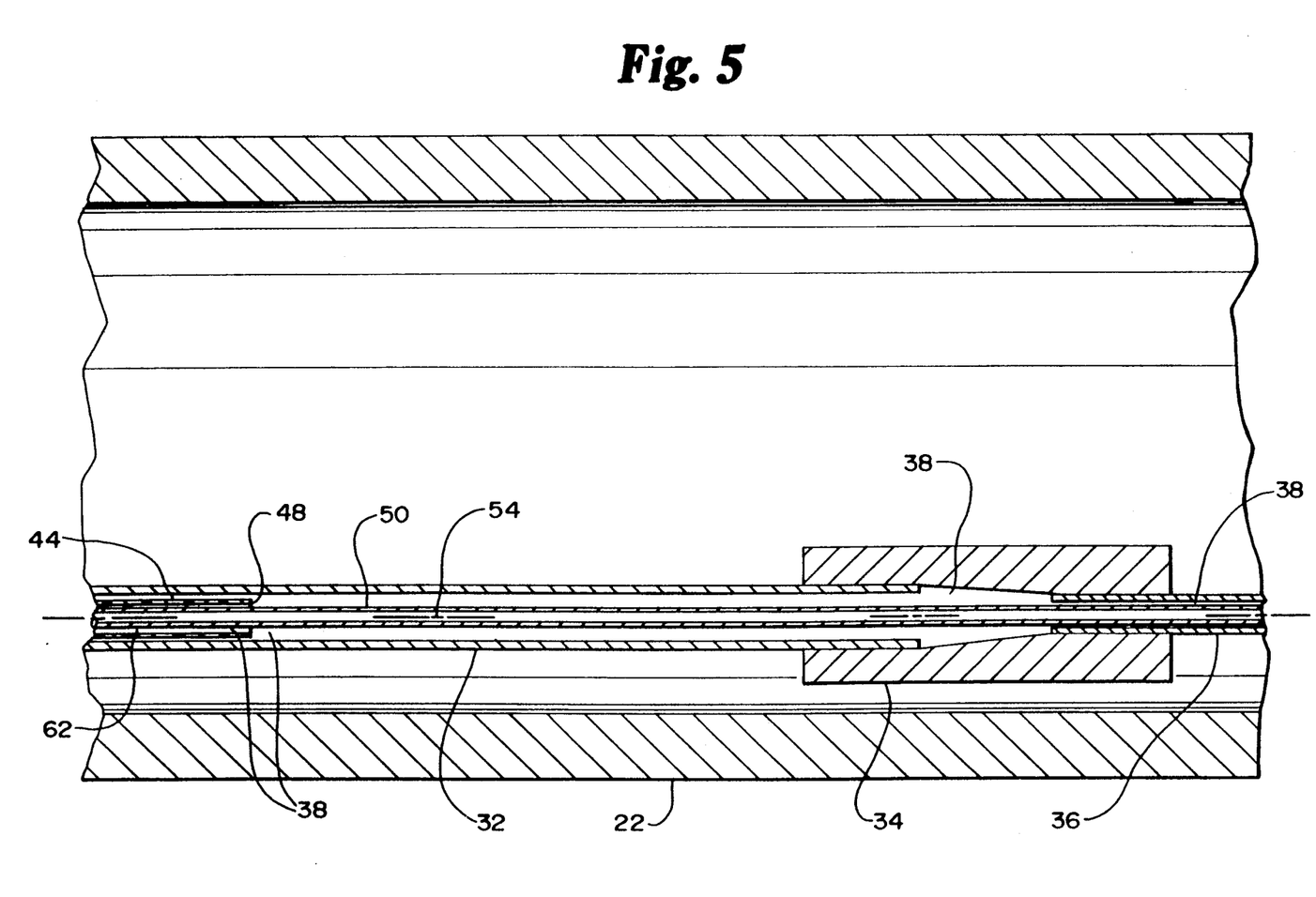
FIG. 5 is a partial exploded longitudinal section through the handle of the first device showing the fluid and laser fiber guide tube, Teflon coaxial fluid delivery tube and channel, and laser fiber.
Figure 6:
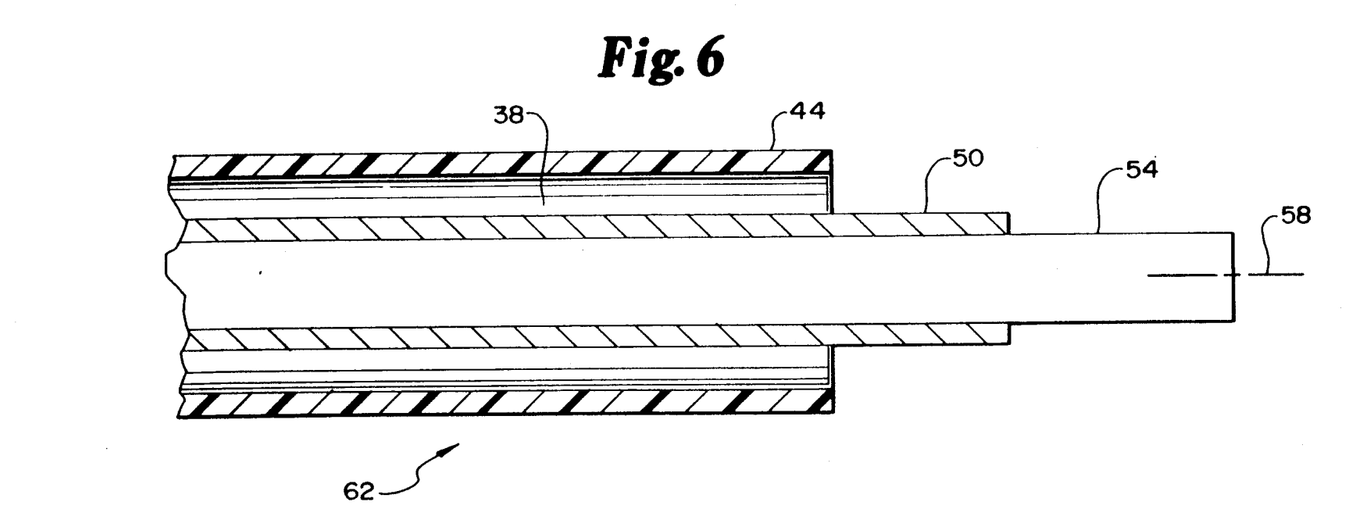
FIG. 6 is a partial exploded longitudinal section of the first laser fiber optic delivery system with Teflon coaxial fluid delivery tube.

As illustrated in FIGS. 1, 2, 3, 4, 5 and 7, a fluid and laser fiber guide tube extends longitudinally within the first soft tissue aspiration device from the proximal handle end cap 26, at the laser energy source port 41, terminating at a point 40 immediately proximal to the soft tissue aspiration inlet port 20. The fluid and laser fiber guide tube consists of the coaxial fluid channel 30 drilled in the proximal handle end cap 26, the fluid and laser fiber large guide tube 32, the guide tube transition coupler 34, and the fluid and laser fiber small guide tube 36. The large guide tube 32 is of sufficient internal diameter (about 0.094") to accommodate the Teflon coaxial fluid delivery tube 44 (FIGS. 4, 5 and 6). The small guide tube is of sufficient internal diameter (about 0.054") to accommodate the Teflon laser fiber sheath 50 and laser fiber 54 and to provide clearance for the coaxial fluid channel 38 (FIGS. 3, 4 and 5). The guide tube transition coupler 34 is positioned within the handle 22 proximal to the proximal end of the cannula 16 and is drilled to accommodate the external diameters of the large 32 and small guide tubes 36. The guide tube components are joined together and to the proximal handle end cap 26 and within the aspiration cannula inner wall utilizing a means such as soldering or welding. The fluid and laser guide tube is provided with an O-ring seal 46 at its retention within the proximal handle end cap 26 at the laser energy source port 41.

Housed within the fluid and laser fiber guide tube is the laser fiber optic delivery system 62, shown in FIGS. 1, 2, 3, 4, 5 and 6, and consists of the Teflon coaxial fluid delivery tube 44, the Teflon laser fiber sheath 50, and the laser fiber 54, having laser discharge axis 58. The Teflon coaxial fluid delivery tube 44 is connected to a saline fluid source and pump integral with the laser energy source (not shown) and passes into the proximal end cap of the handle 16, through the fluid and laser guide channel 30 into the large guide tube 32, terminating at a point 48 within the large guide tube. The large guide tube 32 is maintained in position within cannula 12, for example, by silver solder through holes 37, as illustrated in FIGS. 2 and 3. The Teflon coaxial fluid delivery tube delivers cooling and irrigating fluid into the fluid and laser large guide tube 32, the fluid passes distally within the guide tube 32 surrounding the Teflon laser fiber sheath 50 and laser fiber 54 to the terminal point of the small guide tube 36. The laser fiber 54 constitutes the laser energy transmitting means, extending from the laser energy source (not shown), through the energy source port 41 to a terminal point 56 immediately prior to the terminal point of the fluid and laser fiber guide tube 40. The retention of the laser fiber optic system 62 is accomplished by a retaining screw 42 at the fluid and laser energy source port 41.

Figure 8:
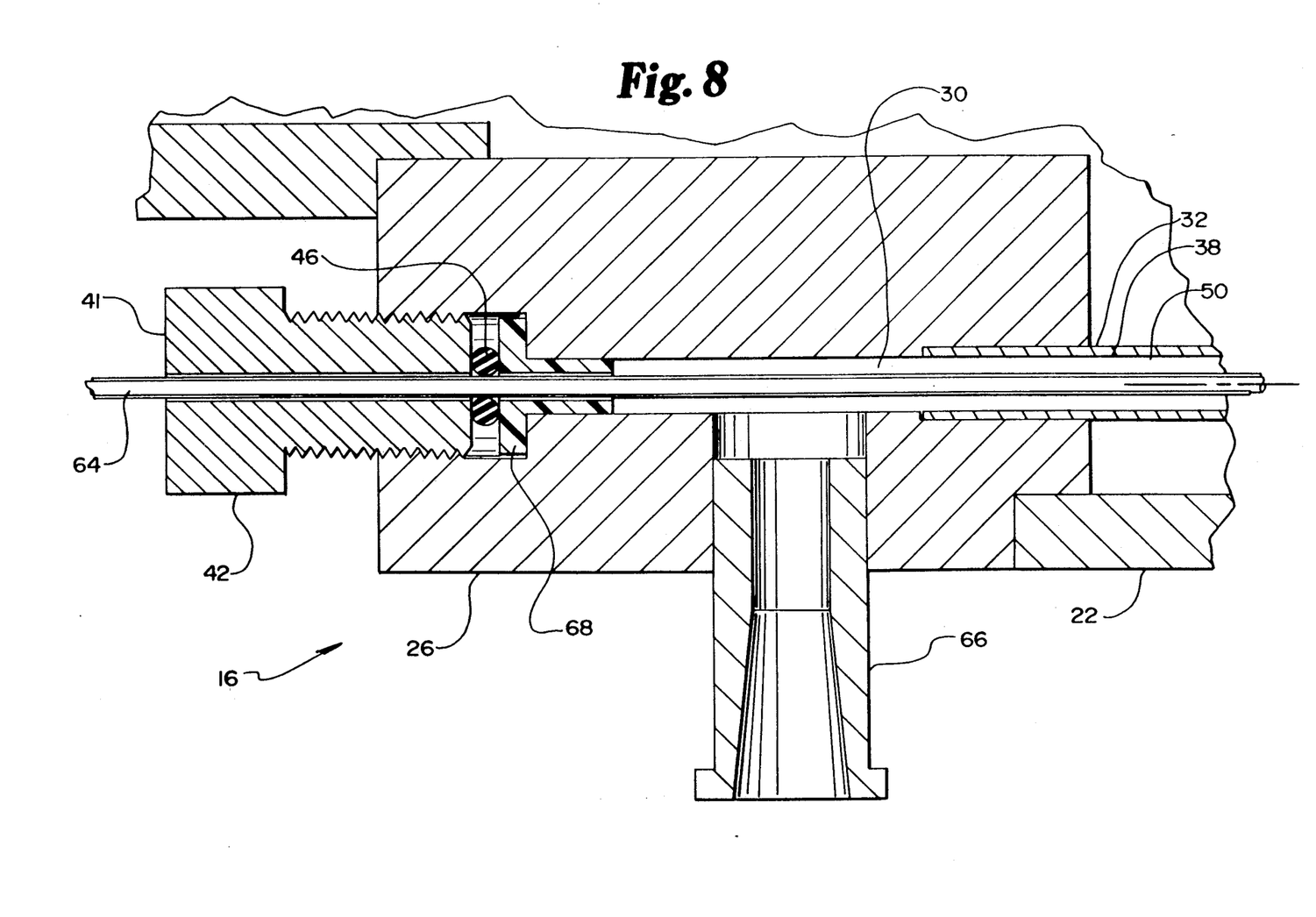
FIG. 8 is a partial exploded longitudinal section view of the handle and proximal end cap of the first device showing the attachments of the fluid and laser guide tube to the alternative fiber optic delivery system and source of fluid.
Figure 9:
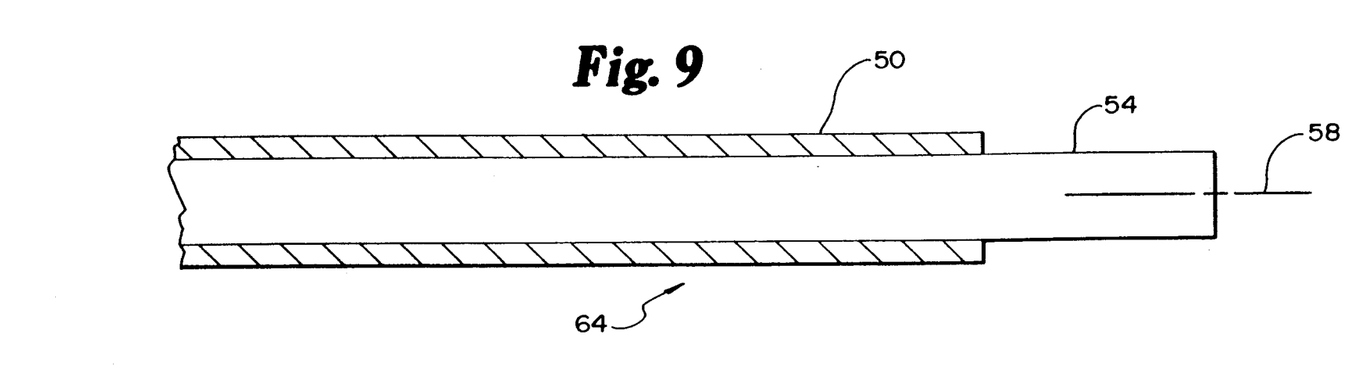
FIG. 9 is a partial exploded longitudinal section of an alternative laser fiber optic delivery system without Teflon coaxial fluid delivery tube.

FIGS. 7, 8 and 9 illustrate minor modifications of the preferred configuration of the present invention which allow the soft tissue aspiration cannula to accommodate an alternative fiber optic delivery system 64 (FIG. 9) which does not incorporate a Teflon coaxial fluid delivery tube. A bushing 68 is positioned within the fluid and laser guide channel 30 to allow a fluid and air-tight seal at the fluid and energy source port 41. An optional fluid delivery port 66 is provided to allow the passage of cooling and irrigating fluid from a fluid source and pump (not shown). This port 66 is fitted with a fluid and air tight plug 60 when the Teflon coaxial fluid delivery tube is used.

As will be apparent to those skilled in this art, a shorter and thinner soft tissue aspiration cannula 12 will be useful in more restricted areas of the body, as under the chin, and a longer and larger diameter cannula will be useful in areas such as the thighs and buttocks where the cannula may be extended into soft tissue over a more extensive area. The length of the fluid and laser small guide tube 36 is determined by the length of the soft tissue aspiration cannula 12.

To perform the method of the present invention as illustrated in FIG. 10, the surgeon determines the location and extent of soft tissue to be removed. The appropriate size laser soft tissue aspiration device 10 is selected. A short incision is made and the cannula tip 18 and the distal end of the cannula 14 is passed into the soft tissue to be removed. The fluid delivery pump is activated, delivering normal saline through the Teflon fluid delivery tube 44, into the coaxial fluid channel 38, to the terminal point of the fluid and laser fiber guide tube 40. The application of a fluid flow of normal saline along the fiber to the fiber tip serves to cool the laser fiber 54 and maintain the terminal point of the laser fiber 56 and terminal point of the laser guide tube 40 free of tissue and other detritus. The aspiration pump is then activated. The negative pressure thus generated is transmitted to the laser soft tissue device 10 via a flexible suction tubing, to the soft tissue outlet port 28, through the handle 22, through the cannula 12, to the soft tissue aspiration inlet port 20. The resultant negative pressure thus generated is transmitted to the laser soft tissue device 10 via a flexible suction tubing, to the soft tissue outlet port 28, through the handle 22, through the cannula 12, to the soft tissue aspiration inlet port 20. The resultant negative pressure at the inlet port draws a small portion of the soft tissue into the lumen of the cannula 12, into the path of the laser discharge axis 58. The laser is then activated. The laser energy is transmitted to the terminal point of the laser fiber 56 and into the soft tissue within the cannula lumen, cleaving the soft tissue and coagulating small blood vessels. Additional soft tissue enters the soft tissue inlet port 20 by virtue of a reciprocating longitudinal motion of the laser soft tissue aspiration device 10 within the soft tissue. This reciprocating motion is applied by the surgeon's hand on the handle 22. The reciprocating motion of the laser soft tissue aspiration device, with respect to the surrounding soft tissue, is facilitated by the stabilization of the soft tissue by the surgeon's other hand placed on the skin overlying the cannula soft tissue inlet port 20. Soft tissue is removed from the vicinity of the inlet port 20 to the more proximal portion of the lumen of the cannula, and eventually out the cannula to the soft tissue outlet port 28 by the negative pressure generated by the aspiration pump.

The soft tissue aspiration cannula 12, cannula tip 18, handle 22, distal handle end cap 24, proximal handle end cap 26, aspirated soft tissue outlet port 28, fluid and laser fiber large guide tube 32, guide transition coupler 34, fluid and laser fiber small guide tube, and retaining screw 42 are all preferably of stainless steel. The soft tissue aspiration cannula 12 can be of appropriate sizes such as:

0.312" O.D. × 0.016" wall (0.280" I.D.)
0.250" O.D. × 0.016" wall (0.218" I.D.)
0.188" O.D. × 0.016" wall (0.156" I.D.)
0.156" O.D. × 0.016" wall (0.124" I.D.)

all of variable length. As will be apparent to those of skill in this art, a shorter and thinner diameter aspiration cannula will be useful in more restricted areas of the body, as around small appendages, and a longer and larger diameter cannula will be useful in areas, such as the thighs and buttocks, where the cannula may be extended into fatty tissue over a more extensive area. The cannula tip 18 is in sizes of the same diameter as the aspiration cannula O.D., machined to a blunt tip and to fit the cannula inside diameter. The handle 22 is preferably of tubing of 1.125" O.D.×0.125" wall (1.0" I.D.) about 3.25" long. The distal handle end cap 24 is preferably of 1.125" diameter, machined to fit the handle inside diameter and drilled to accommodate the aspiration cannula outside diameter. The proximal handle end cap 26 is preferably of 1.125" diameter, machined to fit the handle inside diameter, drilled to accommodate the aspiration outlet port, fluid and laser guide channel, and large guide tube, and drilled and tapped to accommodate the retaining screw. The aspirated soft tissue outlet port 28 is preferably of 0.75" diameter, machined to fit the proximal handle end cap and tapered to accommodate u ⅜" I.D.×½" O.D. suction tubing, and drilled to a 0.3125" diameter hole. The fluid and laser fiber large guide tube 32 is preferably 0.120" O.D.×0.013" wall (0.094" I.D.), about 2" long. The guide tube transition coupler 34 is preferably 0.25" diameter 0.625" long, drilled to accommodate large and small guide tubes 32 and 36. The fluid and laser fiber small guide tube 36 is preferably of 0.072" O.D. ×0.009" wall (0.054" I.D.) in variable lengths, determined by the length of the cannula 12. Retaining screw 42 is preferably ¼"-28 threads-/inch Allen head cap screw 0.75" long, drilled to accommodate the laser fiber optic delivery system. Plug 60 for fluid source port 66 is preferably a Luer-Lock male plug. The preferred laser fiber optic delivery system 29 is available from, for example, Surgical Laser Technologies, Malvern, Pa., Model number: SFE 2.2

2.2 mm (0.086") O.D. Teflon coaxial fluid delivery tube
0.8 mm (0.315") O.D. Teflon laser fiber sheath
0.600 mm (0.023") diameter laser guide fiber length 4.0 meters (157.5")

The alternative laser fiber optic delivery system is available from, for example, Heraeus Laser Sonics, Inc., Santa Clara, Calif., model number: B24D 0.8 mm (0.315") O.D. Teflon laser fiber sheath
0.600 mm (0.023") diameter laser guide fiber length 3.66 meters (144")

Fluid delivery port 66 is preferably a stainless steel female Luer-Lock. Bushing 68 for laser fiber sheath 50 is preferably of Teflon 0.120" O.D. ×0.072" I.D., 0.187" diameter flange, 0.5" long, approximate dimension.

A preferred laser source for use with preferred device 10 of this invention is available, for example, from Surgical Laser Technologies, Malvern, Pa., model number SLT CL60, power delivery 0 to 40 watts, with a fluid delivery pump. An alternative laser source for use with alternative device 70 of this invention is available, for example from Cooper Laser Sonics, Inc. Santa Clara, Calif., model number: 800, power delivery 0 to 100 watts. The suction tubing is available, for example, from Dean Medical Instruments, Inc. Carson, Calif., preferably ⅜" I.D.× ⅝" O.D. The vacuum aspirator can be of any suitably type, such as that available from Wells Johnson Co., Tucson, Ariz., model: General Aspirator, vacuum 0 to 29+ CFM. The fluid pump for delivering the cooling and cleaning lavage can be of any suitable type, such as an IVAC Volumetric Infusion pump, Model No. 590, available from IVAC Corporation, San Diego, Calif.

B. The Side Cutting or Oblique Cutting and End Cutting Soft Tissue Aspiration Devices; FIGS. 11-16.

DETAILED DESCRIPTION OF THE INVENTION

Figure 11:
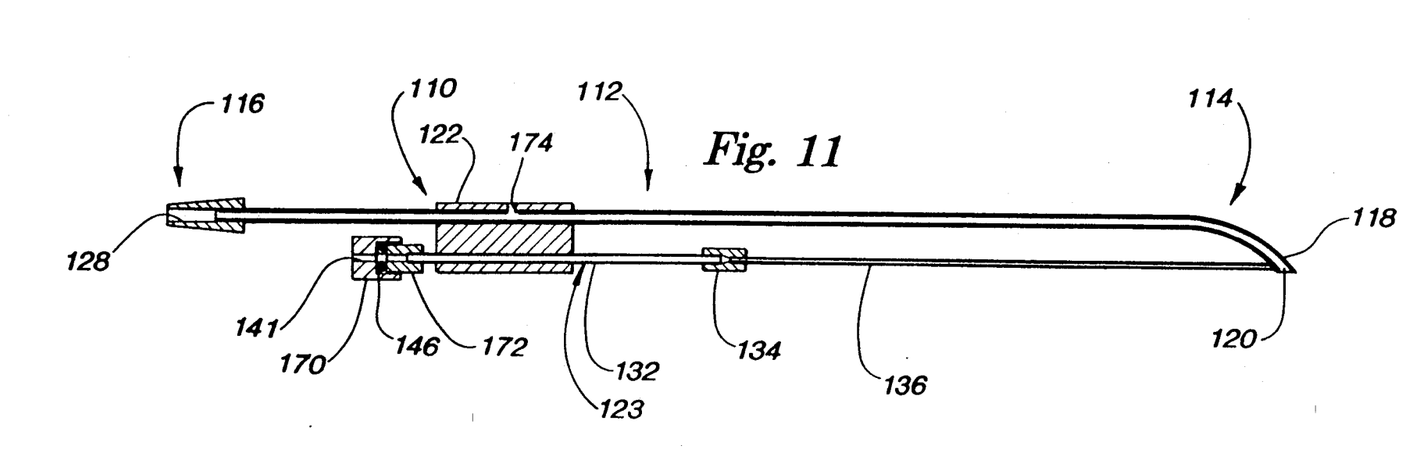
FIG. 11 is a side cut-away elevation view of a side cutting neurological soft tissue aspiration embodiment of the present invention.
Figure 12:
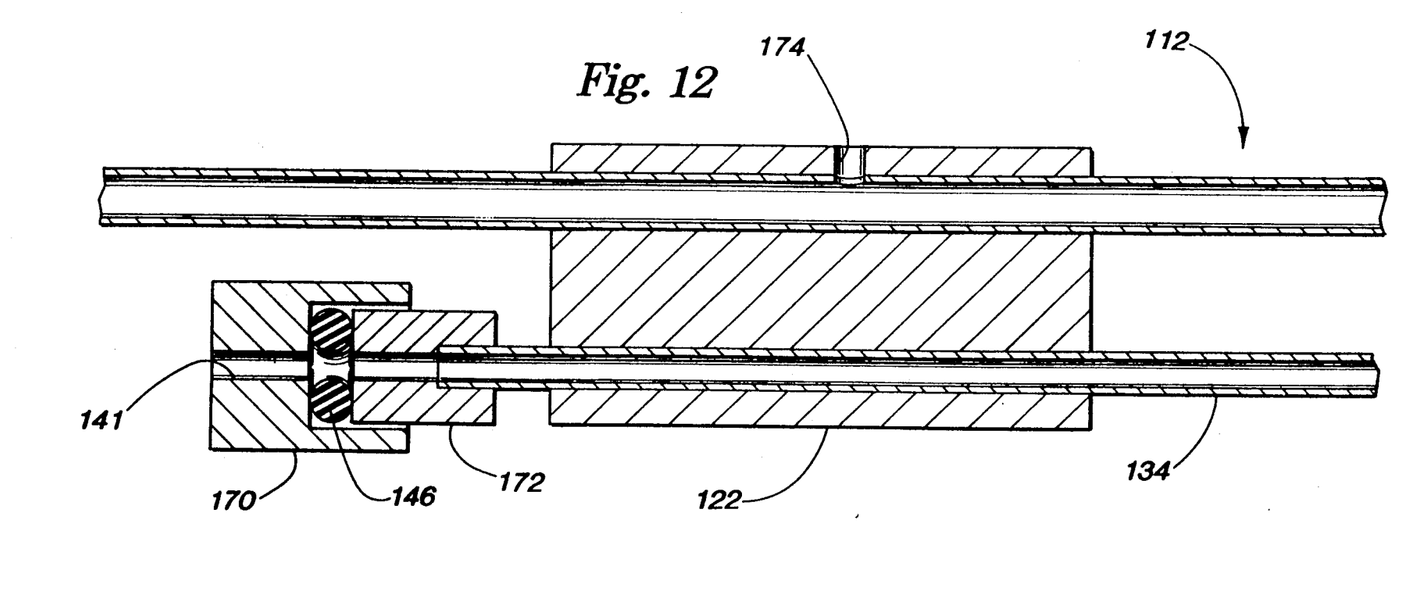
FIG. 12 is a partial exploded longitudinal section view of the handle of the device of FIG. 11 showing the fluid and laser fiber guide tube and the fluid and laser energy source port.
Figure 13A:
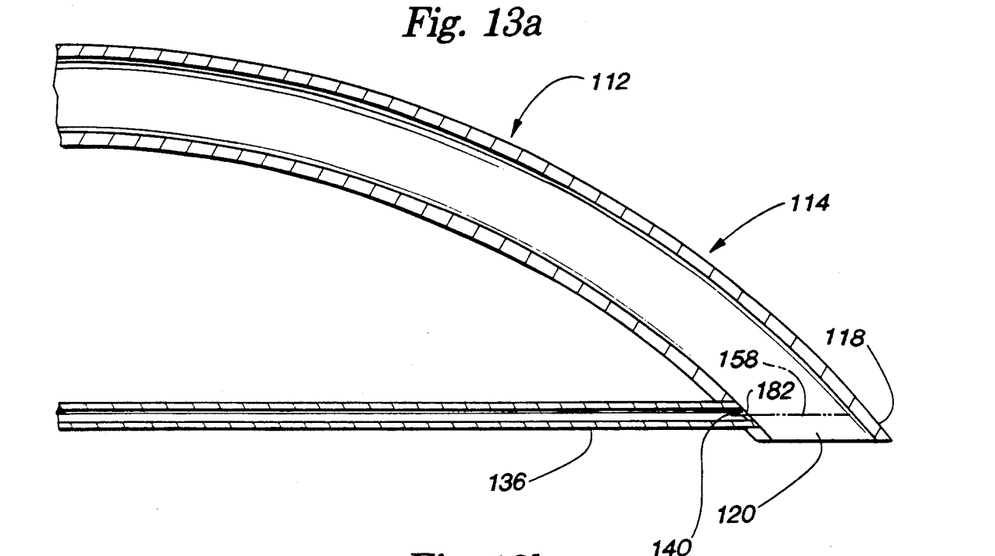
FIGS. 13(a) and 13(b) are partial exploded longitudinal section view of the distal end of the cannula of the device of FIG. 11.
Figure 13B:
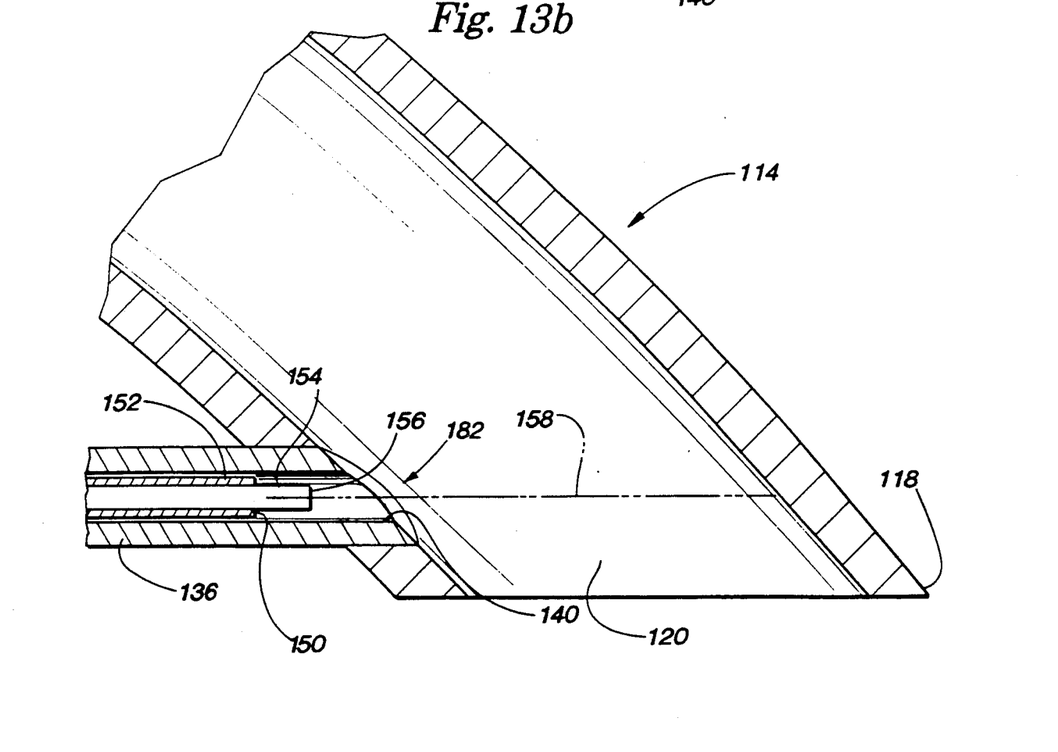

FIG. 11 illustrates a side cutting or oblique cutting laser neurosurgical soft tissue aspiration embodiment of my invention. A neurological soft tissue aspiration device 110 includes an aspiration cannula 112 having a soft tissue inlet port 120 adjacent to a distal end 114 of cannula 112 and a cannula tip 118. FIG. 13 illustrates the cannula tip 118, in which is located the soft tissue inlet port 120 and a cannula side port 182. The device 110 also includes a handle 122 which has a suction control port 174 located in the cannula 112 and the handle 122 (FIG. 12). As illustrated in FIGS. 11 and 13, the cannula has a curved distal end 114 and the cannula tip 118 is cut at an angle which best allows access to excise soft tissue in a direction transverse to the major axis of cannula 112. FIG. 11 illustrates the cannula's proximal end 116, which includes a soft tissue outlet port 128 for aspirating tissue. Soft tissue outlet port 128 is connected to an aspiration source by a plastic tubing (not shown).

As illustrated in FIGS. 11, 12 and 13, a fluid and laser fiber guide tube 123 extends longitudinally from the proximal end of the cannula 116, through the handle 122 and terminating at a point 140 in the cannula side port 182. The guide tube 123 consists of a large fluid and laser fiber guide tube 132 secured in the handle 122, a guide tube transition coupler 134 and a small fluid and laser fiber guide tube 136. Small guide tube 136 is of sufficient internal diameter to accommodate a Teflon laser fiber sheath 150 axially surrounding a laser fiber 154 (FIG. 13). As shown in FIG. 11, the transition coupler 134 is drilled to accommodate the external diameters of the large 132 and small 136 guide tube and is positioned between them. The guide tube components are joined together by coupler 134 utilizing a suitable means such as soldering or welding. Small guide tube 136 is joined to the cannula distal end 114 at the cannula side port 182 and large guide tube 132 is joined to the handle 122 utilizing a means such as soldering or welding. The large guide tube 132 is operatively coupled to a laser energy and fluid flow source (not shown) using a male fitting 172, which communicates with a female retaining nut 170 having an 0-ring seal 146 between fitting 172 and nut 170 (FIG. 11, 12). Nut 170 and fitting 172 axially surround a fluid and laser energy source port 141 for admitting fluid flow from the fluid flow source and mating the laser fiber 154 with the laser energy source (FIG. 11, 12).

Housed within guide tube 123 is laser fiber 154 which is axially surrounded by sheath 150 (FIG. 13). Fiber 154 constitutes the laser energy transmitting means, extending from laser energy source (not shown), through port 141 to a terminal point 156 adjacent to a terminal point of the fluid and laser fiber guide tube 140. Sheath 150 terminates at a point 152 just prior to the terminal point of fiber 156. Laser energy, from the laser energy source, cleaves soft tissue located in the aspiration port 120 along a laser discharge axis 158 which is a continuation of the longitudinal axis of fiber 156. The cannula 112, large guide tube 132 and small guide tube 136 are positioned such that the laser discharge axis 158 is contained within the distal end of the cannula 114.

Soft tissue is drawn into the aspiration port 120 at which time laser energy contacts the soft tissue along axis 158 and begins to cleave the soft tissue. Subsequently, combined mechanical action of suction at aspiration port 120, from the aspiration source, and cleavage of soft tissue along axis 158 removes soft tissue. Fluid from the fluid flow source flows through guide tube 123, in contact with sheath 150, through side port 182 and into the distal end 114 for cooling fiber 154 and helping to effectuate aspiration of soft tissue.

As will be apparent to those skilled in this art, cannula 112 and guide tubes 132 and 136 can be curved to varying degrees while containing the laser discharge axis 158 entirely within the cannula. This results in the ability to aspirate tissues at different angles.

Figures 14, 16:
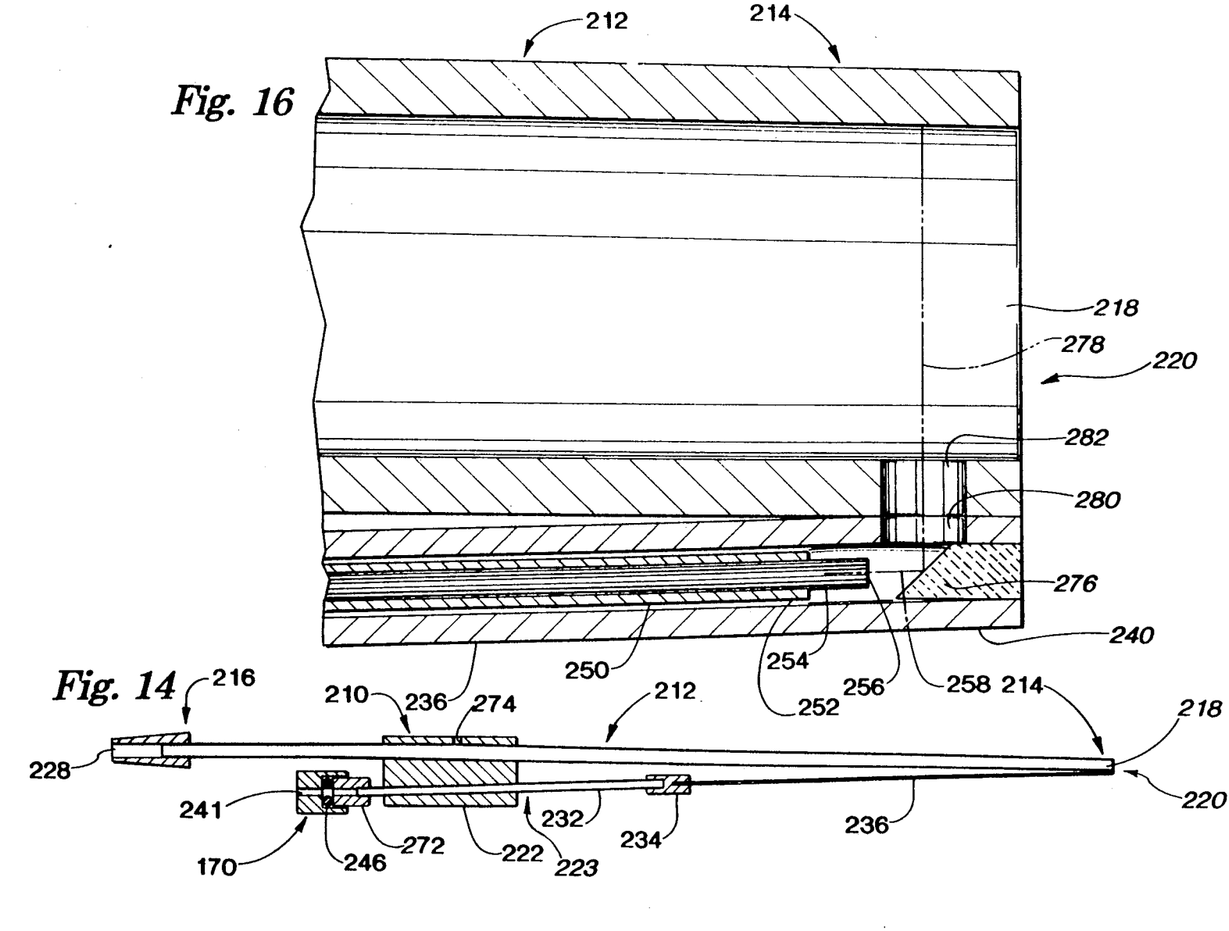
FIG. 14 is a side cut-away elevation view of an end cutting neurological soft tissue aspiration embodiment of the present invention.
FIG. 16 is a partial exploded longitudinal section view of the distal end of the cannula of the device of FIG. 14 showing the laser fiber guide tube and reflecting means.
Figure 15:
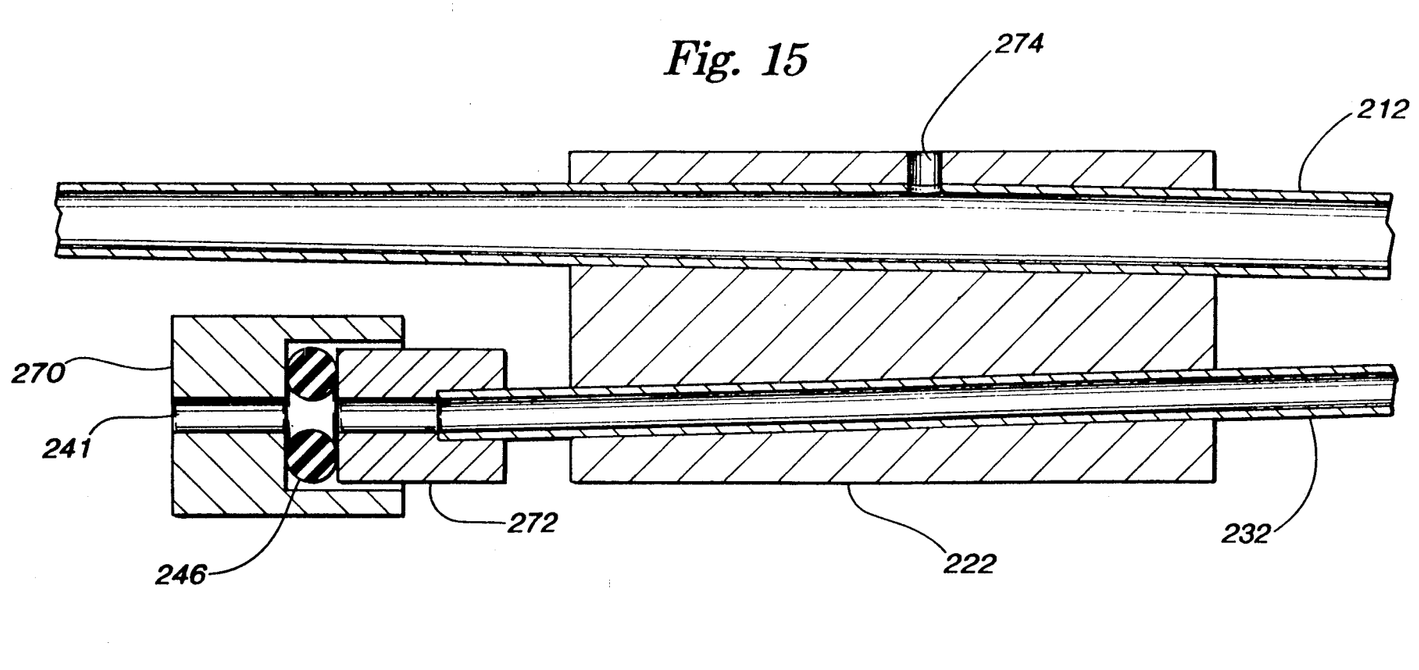
FIG. 15 is a partial exploded longitudinal section view of the handle of the device of FIG. 14 showing the fluid and laser fiber guide tube and energy source port.

FIGS. 14, 15 and 16 illustrate an end cutting laser neurosurgical soft tissue aspiration embodiment of my invention. A neurological soft tissue end cutting and aspiration device 210 includes an aspiration cannula 212 having a soft tissue inlet port 220 adjacent to a distal end 214 and cannula tip 218. FIG. 16 shows the cannula tip 218, which consists of the soft tissue inlet port 220, and cannula side port 282. The device 210 also includes a handle 222 and a suction control port 274 located in the cannula 212 and the handle 222. As illustrated in FIG. 14, the cannula has a proximal end 216 and a soft tissue outlet port 228 for aspirating tissue. Outlet port 228 is connected to an aspiration source by a plastic tubing (not shown).

As illustrated in FIGS. 14, 15 and 16, a fluid and laser fiber guide tube 223 extends longitudinally from the proximal end of the cannula 216, through the handle 222 and terminating at a point adjacent to the cannula tip 218. Guide tube 223 consists of a large fluid and laser fiber guide tube 232 mounted in handle 222, a guide tube transition coupler 234, a small fluid and laser fiber guide tube 236 and a reflecting means 276. Small guide tube 236 is of sufficient internal diameter to accommodate a Teflon laser fiber sheath 250 axially surrounding a laser fiber 254 (FIG. 16). Coupler 234 is drilled to accommodate the external diameters of the large 232 and small 236 guide tubes and is positioned between them. The guide tube components are joined together by coupler 234 utilizing a suitable means such as soldering or welding. Guide tube 236 contains a side port 280 located adjacent to its terminal point 240. Guide tube 236 is joined to the cannula distal end 214 at its terminal point 240 and large guide tube 232 is joined to the handle 222 utilizing a suitable means such as soldering or welding. Side port 280 is located axially in line with side port 282. Reflecting means 276 is located in guide tube 236 adjacent terminal point 240 and joined to the small guide tube 236 utilizing a means such as soldering or welding. The reflecting means 276 comprises a mirror or a solid rod polished to reflect laser energy. Guide tube 232 is attached to the laser energy and fluid flow source using a male fitting 272, which communicates with a female retaining nut 270 having a O-ring seal 246 between fitting 272 and nut 270 (FIG. 14, 15). Nut 270 and fitting 272 axially surround a laser energy source port 241 for admitting fluid flow from the fluid flow source and mating the laser fiber 154 with the laser energy source (FIG. 14, 15).

Laser fiber 254 is axially contained within sheath 250 and housed within guide tube 223 (FIG. 16). Fiber 254 constitutes the laser energy transmitting means, extending from the laser energy source (not shown), through port 241 to a terminal point 256 adjacent to guide tube terminal point 240. Laser fiber sheath 250 terminates at a point 252 just prior to the terminal point of the laser fiber 256. The laser energy travels beyond the terminal point of laser fiber 256 along a laser discharge axis 258 which is a continuation of the longitudinal axis of fiber 156. The reflecting means 276 is positioned in order to reflect laser discharge axis 258 along a reflected discharge axis 278. Axis 278 passes through side port 280, side port 282, and into the cannula distal end 114, where it is contained.

Soft tissue is drawn into the aspiration port 220 at which time laser energy contacts the soft tissue along axis 278 and begins to cleave the tissue. Subsequently, combined mechanical action of suction at aspiration port 220 from the aspiration source and cleavage of soft tissue along laser discharge axis 278 removes soft tissue. Fluid from the fluid flow source flows through guide tube 223, in contact with sheath 250, through side port 280 and into the distal end 214 for cooling fiber 256 and helping to effectuate aspiration of soft tissue.

By utilizing the present laser soft tissue aspiration device according to the present method, a variety of advantages are achieved. The ND:YAG laser energy or other fiber delivered laser energy capable of coagulation and cutting will decrease blood loss and render the surgical procedure safer by coagulating small blood vessels in the surgical area. By enabling the cutting of the soft tissue in a straighter line, the scooping, ripping and tearing action characteristic of other devices, will be eliminated, resulting in more precise soft tissue removal, fewer contour irregularities and enhanced satisfaction. With the addition of the cutting action of the laser energy provided by the present invention the rate of removal of unwanted soft tissue is greatly enhanced over that of previous devices and techniques thus decreasing operative time. By completely confining the laser energy safely and efficiently within the lumen of the cannula, these benefits are obtained without fear of peripheral laser thermal damage. The fluid flow, in addition to providing cooling and cleaning of the laser fiber, will prevent tissue adherence to and potential damage to the sensitive laser fiber tip. The fluid flow will also assist in solubilizing and emulsifying the fatty tissue serving to further facilitate aspiration and prevent clogging of the cannula throughout the procedure.

Thus, the present invention provides an improved device for use in surgical removal of soft tissue. Animal studies and clinical procedures to date utilizing the present invention for surgical body contouring by removing fat have demonstrated less bleeding, less postoperative pain and bruising, excellent cosmetic results, and generally a more aesthetic procedure than has been possible with previous soft tissue aspiration techniques.

What is claimed is:

1. An in vivo surgical method of aspirating soft tissue from a patient comprising:
    inserting an aspiration cannula through the patient's epidermis and/or bone structure, such that a distal end of the cannula is positioned in an area of soft tissue, said cannula provided with a central lumen in communication with an aspiration inlet port adjacent to the cannula distal end;
    providing laser energy from a laser energy source to a laser energy transmitting means operatively mounted in a fluid and laser guide tube, said guide tube operatively connected at the guide tube's proximal end to a laser and fluid source which is at a proximate end of the aspiration cannula and said guide tube extending longitudinally along the cannula and terminating at the guide tube's distal end which is at the distal end of the cannula, said laser energy transmitted by the laser energy transmitting means; and
    cleaving soft tissue located in the aspiration inlet port, said laser cleaving combining with mechanical suction from an aspiration source operatively connected to a soft tissue aspiration port at the cannula proximate end; and
    aspirating said soft tissue through said aspiration inlet port and cannula; and
    transmitting fluid through said guide tube in contact with said transmitting means from the proximal to the distal end of the guide tube in order to provide cooling for and cleaning of said laser transmitting means; and
    arranging the cannula and laser transmitting means so that only tissue within said cannula is exposed to operative amounts of laser energy.

2. A soft tissue cutting and aspiration device comprising:
    an aspiration cannula having a proximal and a distal end, the cannula provided with an aspiration inlet port adjacent to the cannula distal end for receiving soft tissue and drawing it into the cannula, and having a lumen provided with connection to an aspiration source at the cannula proximal end;

a fluid and laser guide tube extending longitudinally from a laser energy source at a proximal end of said guide tube which is at the cannula proximal end and terminating at a distal end of said guide tube which is at a point adjacent to the aspiration inlet port; and a laser energy transmitting means operatively mounted within said tube, said laser energy transmitting means operatively coupled to a laser energy source at the cannula proximal end and arranged for delivering laser energy to the laser guide tube termination point;

said tube also operatively coupled to a fluid flow source at the cannula proximal end, said fluid flow in intimate contact with said laser energy transmitting means contained within said guide tube from the proximal to the distal end of said guide tube for cooling said transmitting means and helping to effectuate tissue removal; wherein, said laser energy transmitting means and said cannula are arranged such that only tissue within the cannula is exposed to operative amounts of laser energy from the laser energy transmitting means.

3. A laser neurosurgical side cutting device according to claim 2; wherein, the cannula has a radial side port located adjacent to the distal end of the cannula and wherein;

the distal end of the cannula curves such that the laser guide tube communicates with the cannula through the cannula side port; further wherein, the terminal point of the laser guide tube is located in the cannula side port.

4. A laser neurosurgical side cutting device according to claim 3, wherein the laser guide tube communicates with the cannula such that the laser energy from the laser energy transmitting means travels radial to the soft tissue aspiration inlet port.

5. A laser neurosurgical device according to claim 2, wherein the laser energy source is a neodymium-Yag laser or other fiber delivered cutting and coagulating laser.

6. A laser neurosurgical end cutting device according to claim 2, wherein;

the cannula has a radial cannula side port located adjacent to the distal end of the cannula and wherein;

the fluid and laser guide tube has a side port located adjacent to the terminal point of the guide tube and wherein;

the fluid and laser guide tube has a reflecting means located within the guide tube adjacent the terminal point of the guide tube, for reflecting laser energy from the laser energy transmitting means such that the laser energy passes through the guide tube side port and the cannula side port into the cannula.

7. A laser neurosurgical end cutting device according to claim 6, wherein the fluid and laser guide tube and reflecting means are located within the cannula.

8. A laser neurosurgical end cutting device according to claim 6, wherein the fluid and laser guide tube and reflecting means are mounted exterior to the cannula.

9. A laser neurosurgical end cutting device according to claim 6, wherein the reflecting means is a solid rod polished to a surface finish of 2, or a mirror.

* * * * *